United States Patent
Edwards et al.

(10) Patent No.: US 7,927,099 B2
(45) Date of Patent: Apr. 19, 2011

(54) DENTAL PATIENT ANXIETY AND PAIN MANAGEMENT SYSTEM INCLUDING ISOLATED HAND PIECE INTERRUPT AND RESET

(75) Inventors: Michael Q. Edwards, Union, MO (US); Martin R. D. Brading, Chesterfield, MO (US)

(73) Assignee: M2 Partnership LLC, Union, MO (US)

( * ) Notice: Subject to any disclaimer, the term of this patent is extended or adjusted under 35 U.S.C. 154(b) by 76 days.

(21) Appl. No.: 12/353,958

(22) Filed: Jan. 14, 2009

(65) Prior Publication Data

US 2009/0181348 A1 Jul. 16, 2009

Related U.S. Application Data

(60) Provisional application No. 61/020,877, filed on Jan. 14, 2008.

(51) Int. Cl.
*A61C 17/00* (2006.01)
*A61C 1/02* (2006.01)

(52) U.S. Cl. .......................................... 433/98; 433/80

(58) Field of Classification Search .............. 433/80–89, 433/29, 104, 98–101
See application file for complete search history.

(56) References Cited

U.S. PATENT DOCUMENTS

| | | | |
|---|---|---|---|
| 2,648,043 A | 8/1953 | Grögl et al. | |
| 2,650,990 A | 9/1953 | Woodruff | |
| 3,757,421 A | 9/1973 | Kraft | |
| 4,767,327 A * | 8/1988 | Smithwick et al. | 433/98 |
| 4,810,996 A | 3/1989 | Glen et al. | |
| 4,990,087 A * | 2/1991 | De Rocchis et al. | 433/104 |
| 5,634,790 A * | 6/1997 | Pathmanabhan et al. | 433/29 |
| 5,736,098 A * | 4/1998 | Kerwin et al. | 422/28 |
| 6,010,468 A * | 1/2000 | Grove et al. | 601/23 |

* cited by examiner

*Primary Examiner* — Cris L Rodriguez
*Assistant Examiner* — Yogesh Patel
(74) *Attorney, Agent, or Firm* — Matthews Edwards LLC

(57) ABSTRACT

Disclosed is a dental patient anxiety and pain management system including a patient controllable interrupt device operable by a patient for interrupting a flow of pressurized fluid along a fluid path between a pressurized fluid source to a dental hand piece and for venting the pressurized fluid from a portion of the fluid path between the patient interrupt device and the dental hand piece for reducing the motive force driving the operative element of the hand piece, the fluid flow remaining interrupted until a reset device is operated for allowing the flow of pressurized fluid to resume along the fluid path between the pressurized fluid source and the hand piece.

20 Claims, 7 Drawing Sheets

DENTAL PATIENT ANXIETY AND PAIN MANAGEMENT SYSTEM INCLUDING ISOLATED HAND PIECE INTERRUPT AND RESET

This application claims the benefit of U.S. Provisional Application No. 61/020,877, filed Jan. 14, 2008 and herein incorporates that application by reference.

TECHNICAL FIELD

This invention relates generally to dental equipment control, and more particularly, to a system for managing dental patient anxiety and pain including capability for a patient initiated interrupt of a drilling procedure isolated from a reset capability, wherein drilling ceases almost instantaneously in response to the patient interrupt.

BACKGROUND ART

Most dental patients have some level of anxiety or fear associated with dental procedures, particularly those procedures involving a dental drill. While dental anxiety is common, this anxiety has often risen to the level of fear or even dental phobia in a significant percentage of the population. Dental anxiety, fear, or phobia is most often caused by previous, unpleasant dental experiences resulting in trauma due to physical and/or psychological pain. Other contributing factors include, but are not limited to, feeling trapped, a loss of control, physical pain and the helplessness and vulnerability associated with many dental procedures.

Fear of dental procedures resulting in avoiding the dentist can have adverse physical and emotional consequences. Dental health will certainly suffer, possibly leading to physical and psychological problems, such as loss of self-esteem and even depression. Often patients who avoid regular dental care believe that all dental treatment is painful. In addition, these patients fear the dentist may be unresponsive to their expression of pain, either intentionally or unintentionally, leaving them feeling helpless and in pain.

Testing has shown that patient anxiety is reduced and pain tolerance is increased when the patient has a sense of control over the source of the pain. Accordingly a dentist may be more efficient with a less anxious patient. Previous attempts to alleviate patient anxiety include predetermined signals to the dentist or even paddles the patient could raise to alert the dentist to pain. Glen et al., U.S. Pat. No. 4,810,996 even provides a patient controlled audible alarm indicating a level or degree of pain to the dentist. These systems have proven unsuccessful, in part, because a sudden or erratic movement or loud noise may startle a dentist during a drilling procedure. Further, anticipation of a sudden erratic movement or loud noise would likely increase the anxiety felt by the dentist during such procedures. More importantly, these methods do not address the helplessness felt by patients. Even when a patient does alert the dentist to pain, there is no guarantee the dentist will stop the drilling procedure. The dentist may choose to continue because the procedure is "almost done" thus reducing the sense of security of the patient.

Previous efforts to reduce patient anxiety related to pain and helplessness include a patient interrupt switch. Reference in this regard, Smithwick et al., U.S. Pat. No. 4,767,327, which discloses a patient control mechanism for an air conduit of a dental unit using a three valve mechanism. However, the switch and valve arrangement, as depicted in FIGS. 1 and 3 of this reference, seems to allow undesirable results in some situations and/or in the hands of a nervous patient. For example, a single switch, in the patient's control, has the capability to both turn off and turn on the drill. In other words, in addition to stopping the drill in response to pain, the patient may inadvertently restart the drill at an inopportune moment creating a potentially dangerous situation. Because the valves operate sequentially in response to the patient, there is a small inherent delay between switch actuation and the cessation of rotation of the drill. This delay is caused, in part, as the air pressure is diverted to the second and third valves, and finally the air pressure decays in the line to the drill causing the drill to slow to a stop. The delay may be seen in the system in FIG. 3 of the patent, where it appears that the patient interrupt operates on valve 24, valve 22, and eventually closes valve 20 leaving a positive air pressure along the line that must be dissipated through pedal 16 and dental unit 14 before the drill stops. In addition, the line must repressurize after the system resets which may produce a noticeable delay in restarting the drill. A highly sensitive patient may sense and misinterpret the delay and depress the switch more than one time. A nervous patient may fiddle with the switch unintentionally causing one or more partial or full depressions to the switch. Disruptions to the airflow may create erratic or unpredictable drill rotation and even cause the cycling of power to the drill.

Additionally the Smithwick system appears to pose a significant problem for use with modern dental equipment. Typically the same pressurized air source that provides power to the dental hand piece also provides power to the dental chair and associated equipment. According to FIG. 3 of the Smithwick patent, valve 22 as connected to the compressed air source 18 seems to remove the air source completely. Used with modern dental equipment, the patient interrupt of Smithwick would not only stop the drill, but it would also remove power from the dental chair and associated equipment.

Additional shortcomings of the Smithwick system are related to its complexity and difficulty in implementation. Because the system requires diverting air pressure to numerous locations in the overall dental system, additional tubing must be installed each of the locations. Also the system requires three independent pneumatic valves installed at different locations. Pneumatic valves are sensitive to variations in air pressure at the source and include a decay time as the air pressure bleeds out of the system. As a result, instead of a desirable nearly instantaneous stop in response to the patient input, the drill of the prior art system will likely appear to gradually slow to a stop with the possibility of unintentionally being restarted by the patient.

It is therefore desirable to provide a dental patient anxiety and pain management system which overcomes at least one of the problems, shortcomings or disadvantages set forth above.

SUMMARY OF THE INVENTION

What is disclosed is a dental patient anxiety and pain management system which overcomes at least one of the problems, shortcomings or disadvantages set forth above.

Most dental instruments or hand pieces, such as drills, and the like, are powered by compressed air flowing through a line therebetween. When not in use, the hand piece is placed in one of a plurality of resting places or seats of a housing or tool holder. The housing or tool holder includes a safety switch at each seat that prevents operation of the associated hand piece when placed therein. The dental instrument, when removed from the seat, is typically started and stopped by depressing a foot pedal in the well known manner.

According to the invention, a system for delivering pressurized fluid from a pressurized fluid source to a dental hand piece or drill in a fluid path includes a patient controllable interrupt device disposed in connection with the fluid path and operable by a patient for interrupting the flow of the pressurized fluid along the fluid path from the pressurized fluid source to the hand piece and for venting the pressurized fluid from a portion of the fluid path between the patient interrupt device and the hand piece for reducing the motive force driving the operative element thereof. The system further includes a reset device disposed in connection with the fluid path and operable for allowing the flow of pressurized fluid to resume along the fluid path between the pressurized fluid source and the hand piece.

According to an aspect of the invention, the hand piece includes an inlet port and an exhaust port. Pressurized fluid is delivered to the hand piece through the inlet port, and when the patient controllable interrupt device is operated for interrupting the flow of pressurized fluid along the fluid path, the inlet port will be depressurized.

According to a preferred aspect of the invention, a pneumatic latching valve, actuated to a closed position, by a first input and actuated to an open position by a second input, is disposed in the line with the dental instrument and the actuating foot pedal. In a preferred embodiment of the invention, the first input is received from a first switch, such as a push button, or the like, held by the dental patient. When actuated, the valve latches closed, preventing air flow across the valve and expelling residual air from at least a portion of line. Rotation of the drill is nearly instantaneously halted. The valve remains latched closed and the drill remains stopped until the second input is received from a second switch, such as a push button, or the like, typically controlled by the dentist.

According to another aspect of the invention, the patient input operates the safety switch of the housing seat associated with the hand piece in use by the dentist causing the hand piece to stop. A separate reset switch is placed on the housing to disengage the safety shut off of the housing.

Preferred apparatus of the system includes electromechanical three way pneumatic valves for placement in line with the foot pedal and the hand piece, and mechanical switches, such as push button or push switches for patient input and dentist reset capability. However, other suitable devices or implementations, including, but not limited to, wireless networking may be employed. Implementation of the system is simple and can be incorporated into dental chair and housing designs or installed after market.

As a result of the invention, anxiety may be reduced and the dental patient may even be willing to tolerate more discomfort prior to alerting the dentist, because the patient is confident the procedure will stop when requested. The dentist is able to work more efficiently on a less anxious patient, pain management is more efficient, and dental procedures may be less stressful without the use of sedation or other types of drugs typically used on such patients that alter their state of consciousness and depression of the patients' ability to breathe on their own.

DETAILED DESCRIPTION OF THE INVENTION

Figure 1:
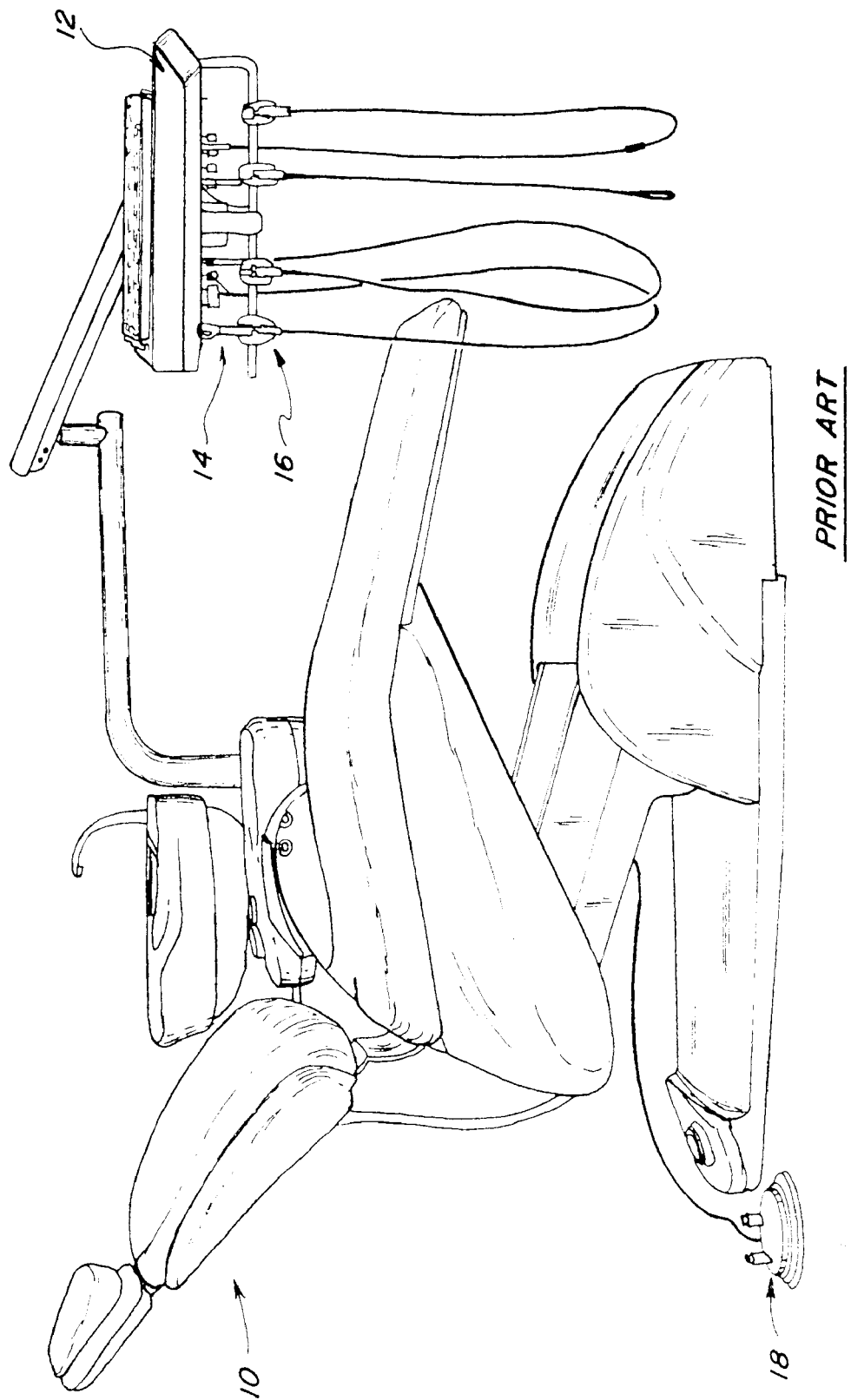
FIG. 1 is a typical dental chair and housing arrangement.
Figure 2:
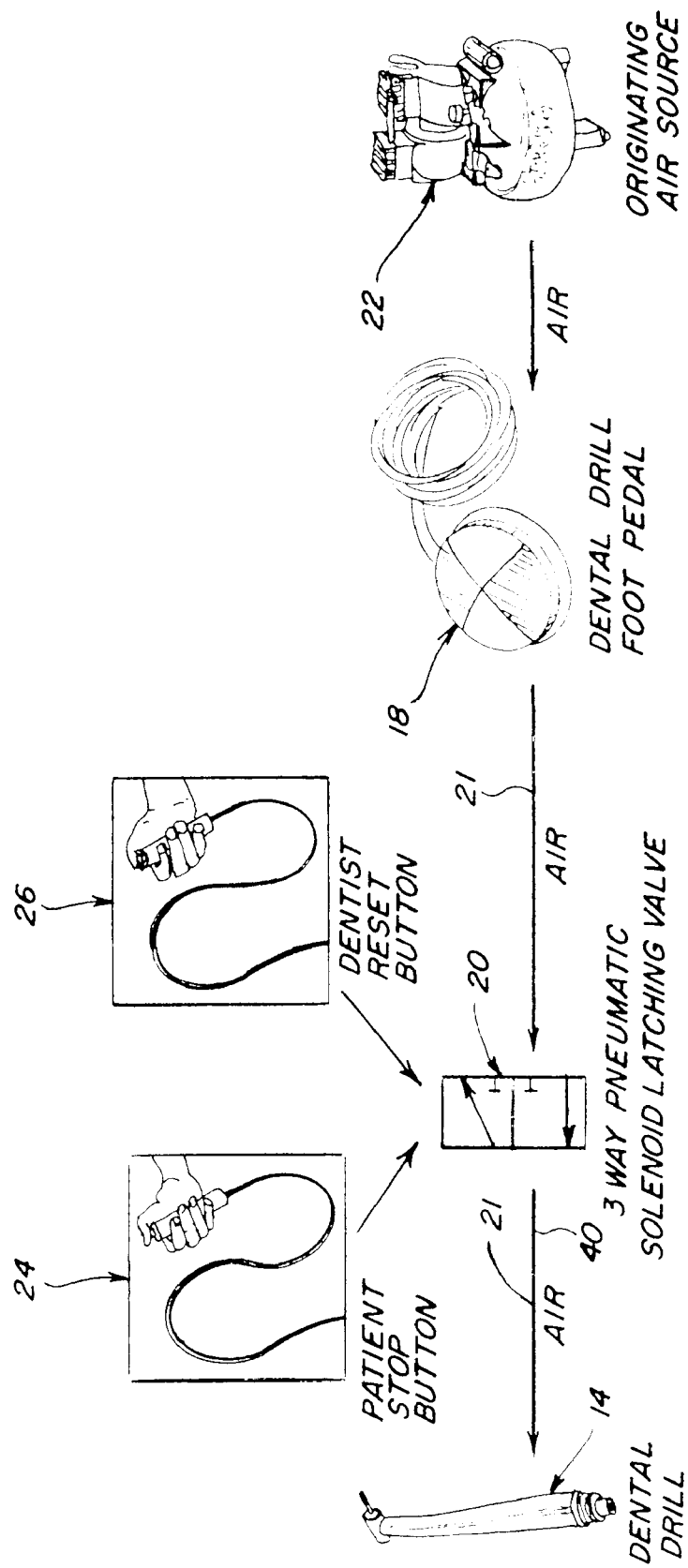
FIG. 2 is a top level diagram of an arrangement of a preferred embodiment of the invention.
Figure 3:
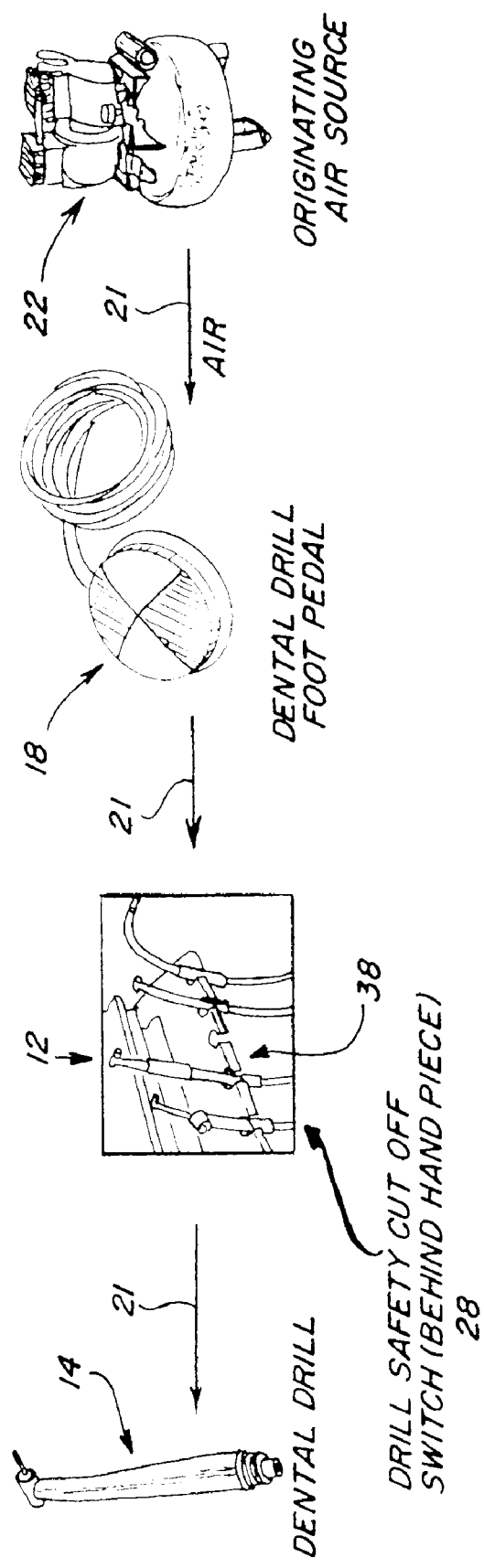
FIG. 3 is a top level diagram of an arrangement of another preferred embodiment of the invention.
Figure 4:
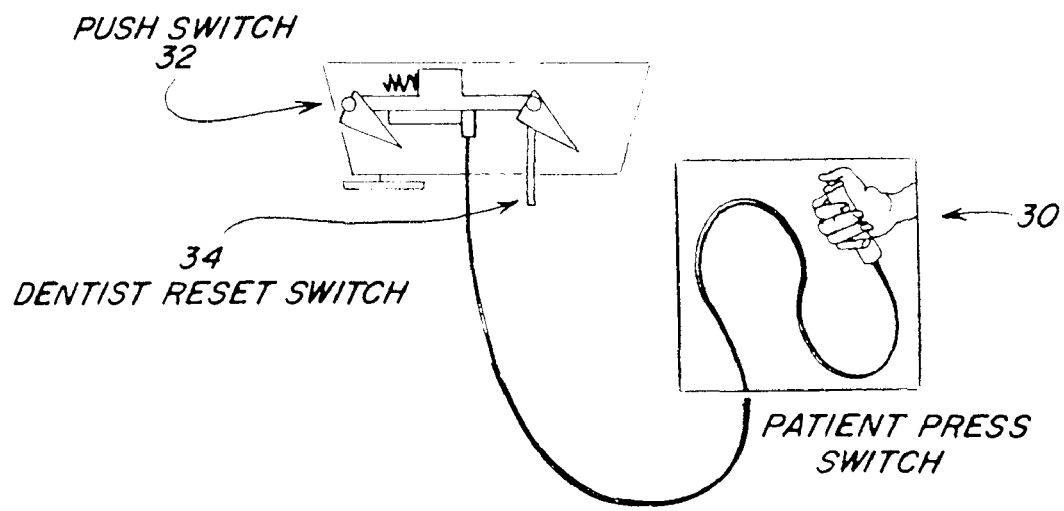
FIG. 4 depicts a push switch in communication with a stop mechanism of the embodiment of FIG. 3.

Referring now to the drawings, wherein like numbers refer to like parts, FIG. 1 represents a typical dental chair 10 and housing or tool holder 12 arrangement as is well known in the prior art. A dental hand piece, such as a drill 14 rests in a seat 16 of tool holder 12 when not in use. Tool holder 12 includes an internal safety shut off mechanism (not shown) that prevents the hand piece or drill 14 from operating when it is placed in seat 16. Hand pieces are powered by a compressed air source (see FIGS. 2 and 3) and actuated when removed from seat 16, by a foot pedal 18 in the usual manner.

With reference to the remaining figures and for purposes of explanation, air and fluid will be used interchangeably, i.e. compressed air/fluid source, pressurized air/fluid, air/fluid path, etc. As seen in FIGS. 2, 3, 6, 7 and 8, a fluid path 21, or air line, extends from a source of pressurized fluid 22 to drill 14. An operator controllable device or foot pedal 18 is disposed in connection with fluid path 21 and operable by an operator for controlling delivery of a flow of a pressurized fluid along fluid path 21 to the drill 14 to provide a motive force for driving an operative element 15 thereof.

According to the invention, a system for delivering pressurized fluid to dental hand piece or drill 14 includes a patient controllable interrupt device 25 disposed in connection with fluid path 21 and operable by a patient for interrupting the flow of the pressurized fluid along fluid path 21 from the pressurized fluid source 22 to the drill 14 and for venting the pressurized fluid from a portion of the fluid path 40 between patient interrupt device 25 and drill 14 for reducing the motive force driving operative element 15 of drill 14. The system further includes a reset device disposed in connection with fluid path 21 and operable for allowing the flow of pressurized fluid to resume along fluid path 21 between pressurized fluid source 22 and drill 14.

Figure 7:
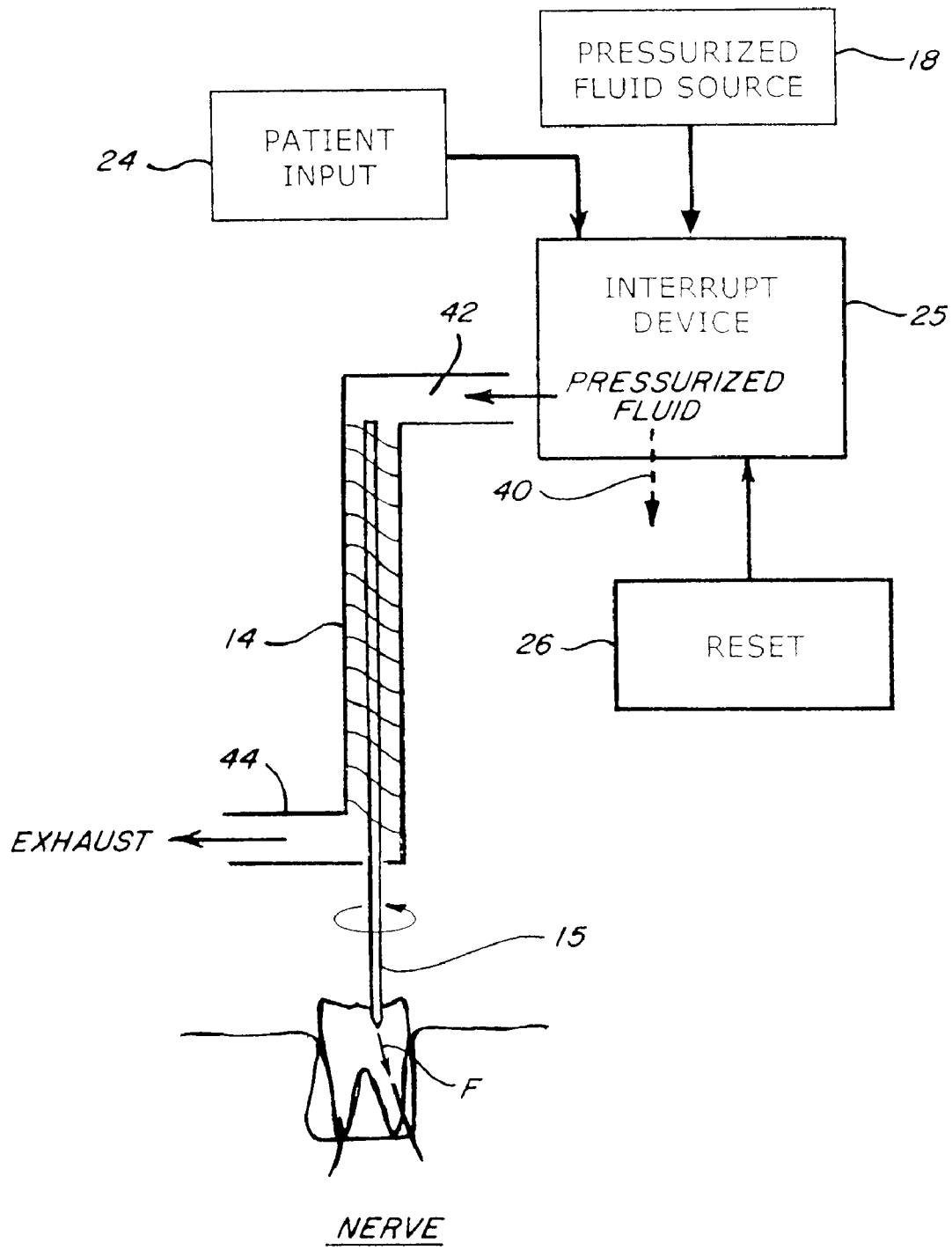
FIG. 7 is a simplified representation of the dental hand tool according to the invention.

According to an aspect of the invention, as shown in FIG. 7, drill 14 includes an inlet port 42 and an exhaust port 44. Pressurized fluid is delivered to drill 14 through inlet port 42, and when patient controllable interrupt device 25 is operated for interrupting the flow of pressurized fluid along fluid path 21, inlet port 42 will be depressurized as indicated by dashed arrow 40 associated with interrupt device 25. Therefore, as the patient senses pain represented by arrow F due to pressure, vibration, heat, or the like generated by operative element 15 of drill 14, the patient input signal to interrupt device 25 will interrupt the fluid path to the device and immediately depressurize inlet port 42. It is important to note that depressurizing inlet port 42 causes operative element 15 of drill 14 to stop much more quickly than known systems because the fluid pressure does not have to dissipate through drill 14 to exhaust port 44.

According to another aspect of the invention, as illustrated in FIGS. 2 and 6-8 a patient input device or a patient stop button 24, is configured so as to be operable by the patient for outputting a patient interrupt signal and a reset input device or dentist reset button 26 is configured so as to be operable for outputting a reset signal. A signal controlled valve 20, also shown as a pneumatic latching valve, is in operative communication with patient stop button 24 and dentist reset button 26 and is disposed in connection with fluid path 21 between foot pedal 18 and drill 14. Signal controlled valve 20 is configured so as to be controllably operable in response to the patient interrupt signal for moving to a first position for interrupting the pressurized fluid flow in the path and diverting at least a portion of the pressurized fluid flow from fluid path 21 and remaining in the first position until the reset signal is received.

As an example, a suitable signal controlled valve 20 may be a valve which may be operated mechanically, electromechanically, electronically, or in another suitable fashion. Other suitable valves include three port electromechanical valves and solenoid valves. The dental patient is supplied with a stop mechanism in the form of patient stop button 24 which may be implemented with a hand held push button in communication with the latching valve. When the patient depress the push button, the latching valve closes interrupting air pressure and expelling air from the line, thereby stopping rotation of drill 14. Drill 14 halts almost instantaneously in response to the loss of air pressure and will not restart, even if foot pedal 18 is depressed or patient stop button 24 is depressed again. Normal functioning of drill 14 will not return until a reset mechanism, depicted here as a dentist reset button 26, in communication with the latching valve, is actuated causing the latching valve to open. The stop mechanism and reset mechanisms are shown in the preferred embodiment mechanically connected to latching valve, but it should be understood that it is contemplated that non-mechanical or wireless communication within a wireless network may also be employed. Further, while patient controllable interrupt device 25 is shown in one embodiment as signal controlled valve 20, it is contemplated that any suitable mechanism for interrupting and venting fluid flow at on the inlet port side of drill 14 may be used.

According to another embodiment of the invention, as illustrated in FIGS. 3-8, a safety stop mechanism or device 28 internal to housing or tool holder 12 is used to stop drill 14 rotation. Foot pedal 18 is disposed in connection with fluid path 21 and operable by an operator for controlling delivery of a flow of pressurized fluid to drill 14 to provide a motive force for driving operative element 15 thereof. A patient press switch 30 is disposed in operative communication with tool holder 12 and operable by the patient for simulating presence of drill 14 in seat 16 of tool holder 12 and engaging safety stop device 28 for reducing the motive force driving operative element 15 of drill 14. A dentist reset switch 34 is disposed in operative communication with tool holder 12 and operable for disengaging safety stop device 28 in absence of drill 14 presence in seat 16.

Figure 5:
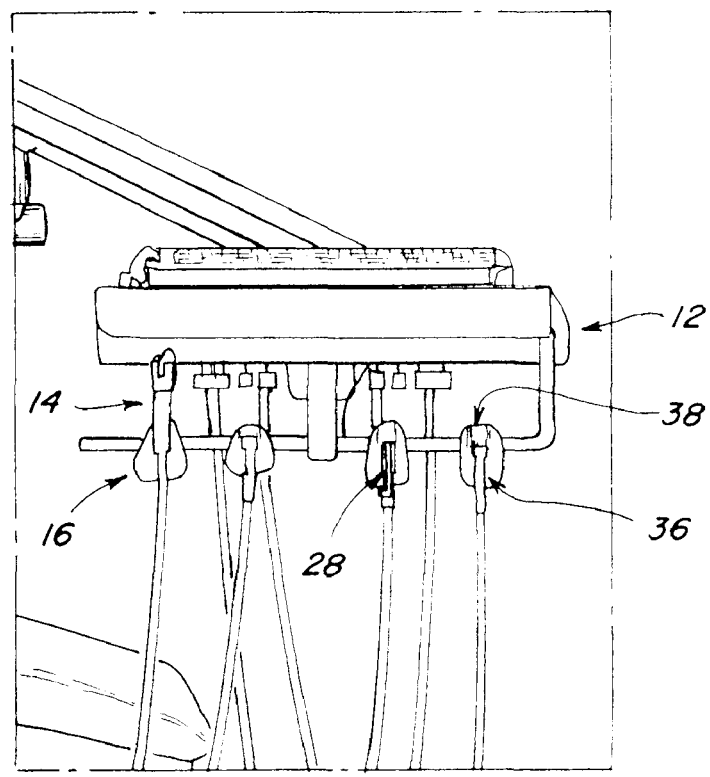
FIG. 5 is a front view of the housing including a dental hand piece.

In one aspect of the invention, a latching mechanism, depicted here as a push switch 32, is installed on housing or tool holder 12 in cooperation with seat 16. FIG. 5 is a front view of a typical tool holder 12 with seats 16, 36. As shown in FIG. 5, seat 16 holds drill 14 and seat 36 is unoccupied. Arrow 38 shows one possible placement of latching mechanism or push switch 32 for the hand piece associated with seat 36 according to the invention.

When the patient depresses hand held push button 30, push switch 32 is positioned to simulate the presence of drill 14 in seat 16 triggering the safety shut off of tool holder 12. Drill 14 stops rotating and remains stopped, even if foot pedal 18 or push button 30 are depressed. Normal operation of drill 14 will not be available until the reset mechanism, depicted in the figure as a lever or dentist reset switch 34, is actuated removing the simulated presence of the hand piece in seat 16. The latching mechanism is depicted as a push switch with a lever reset. It should be understood that it is contemplated that other mechanical or wireless variations are encompassed within the scope of the invention.

Figure 6:
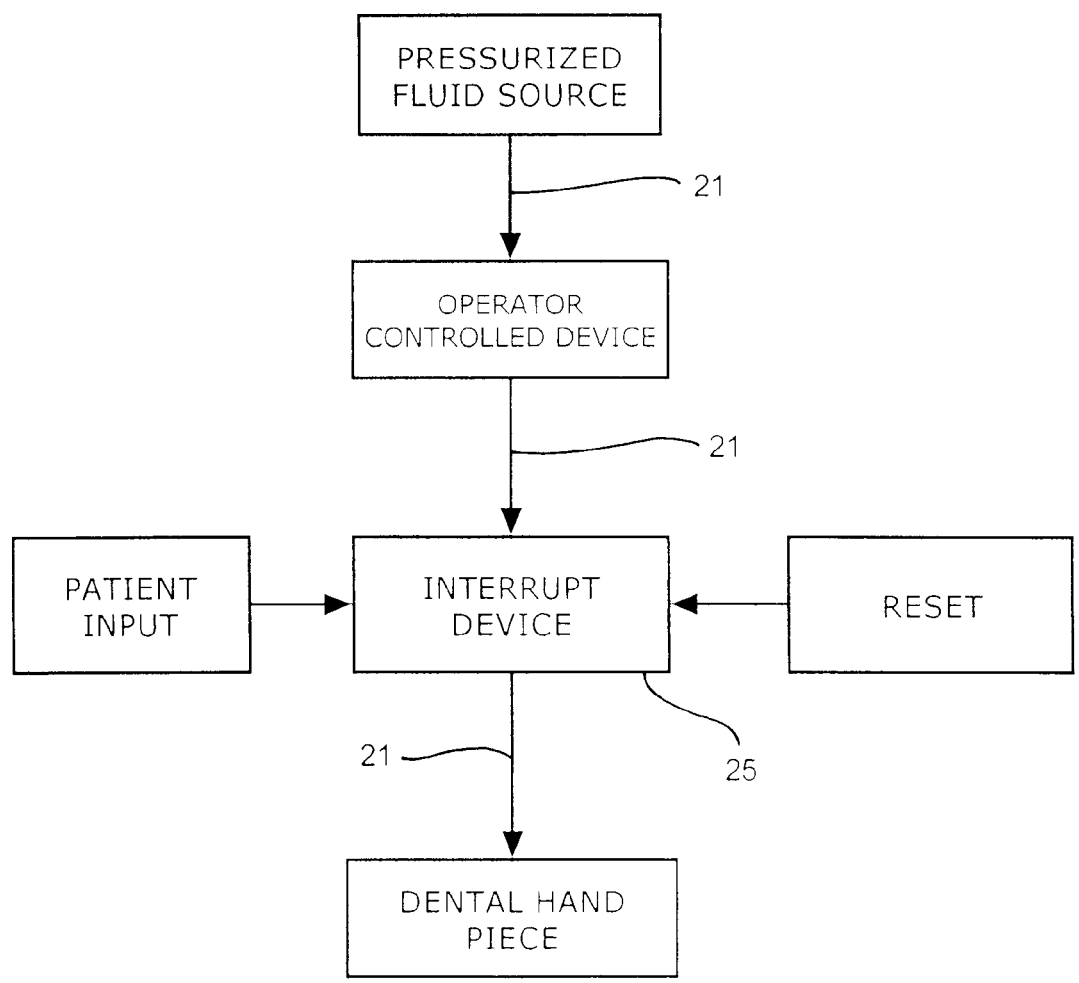
FIG. 6 is a top level diagram of the system of the invention.
Figure 8:
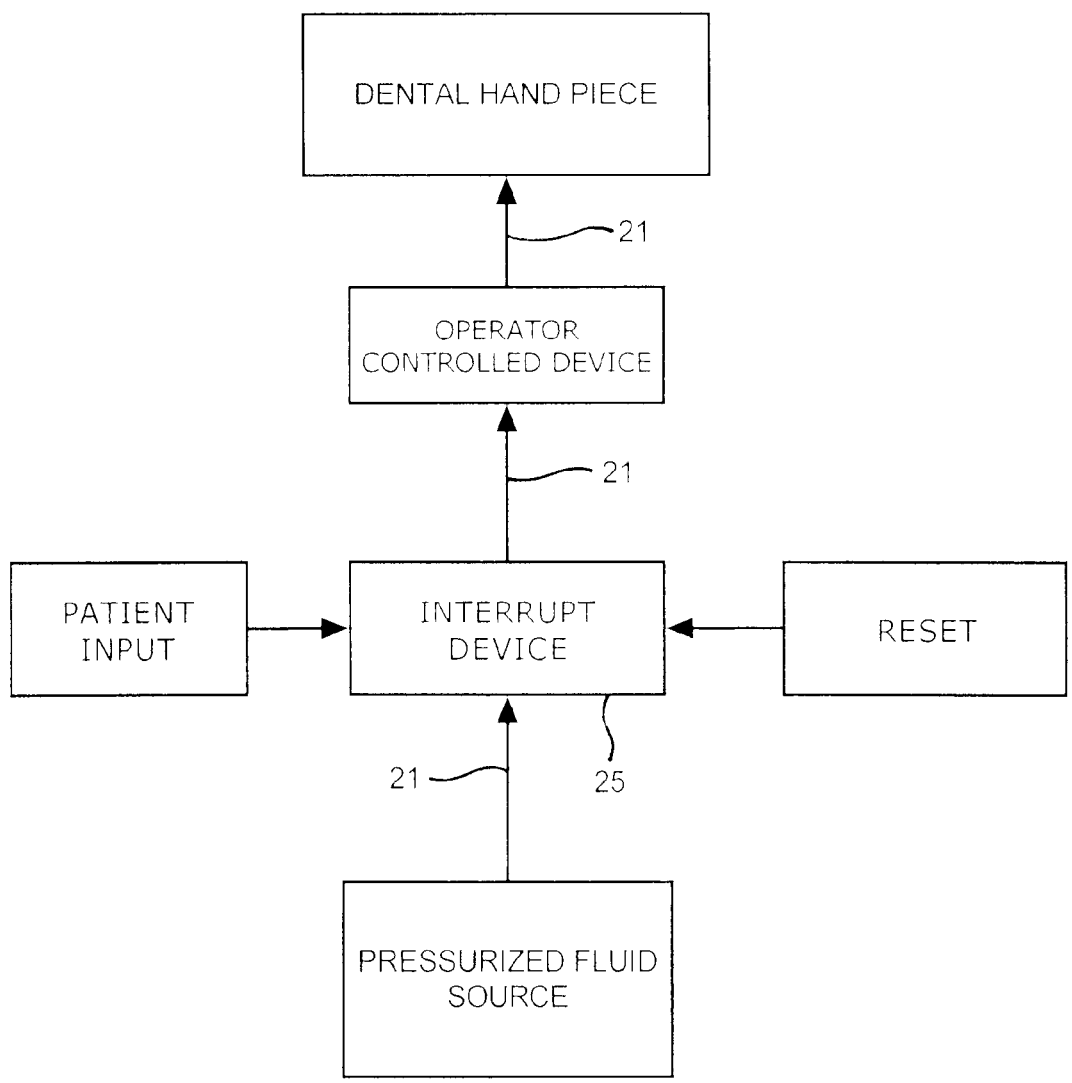
FIG. 8 is a top level diagram of an alternate embodiment of the system of the invention.

FIGS. 6-8 represent simplified block diagram representations of the system of the present invention. FIG. 6 shows patient interrupt device 25 situated between the operator controllable device and the dental hand piece, while FIG. 8 shows an alternate arrangement in which patient interrupt device 25 is situated between the pressurized fluid source and the operator controllable device.

The invention described hereinabove improves upon the safety and reliability of the prior art. An important safety feature of the invention is the isolation of the reset mechanism from the patient. After the patient has stopped the drill, a reset, under the control of the dentist is required to resume normal drill operation. This feature prevents inadvertent restart of the drill by the patient or misinterpretation of the patient input as a variation in the air pressure by the dentist. Another feature of the invention is the binary nature of the latching valve. It is either closed or open and its state is unaffected by variations in air pressure or actuation of any mechanism except the positive reset action. In addition, the speed, precision and reliability of the drill stop is an improvement over the prior art. An inherent delay existed in previous systems, because air flow had to be diverted to multiple valves, and the drill slowed to a stop as the air pressure decayed within the system. The present invention vents or expels air when the stop mechanism is actuated. This will stop the drill far faster than the previous systems.

Another advantage of the invention is the simplicity and efficiency of the design. Only one latching valve is required, and installation requires tapping into an existing line in only one location for one embodiment of the invention. For the other embodiment, the system can be installed on existing housings without tapping into the air line at all. This means that after market installation is simple, fast, and inexpensive.

It will be understood that changes in the details, materials, steps, and arrangements of parts which have been described and illustrated to explain the nature of the invention will occur to and may be made by those skilled in the art upon a reading of this disclosure within the principles and scope of the invention. The foregoing description illustrates the preferred embodiment of the invention; however, concepts, as based upon the description, may be employed in other embodiments without departing from the scope of the invention.

What is claimed is:

1. A system for delivering pressurized fluid to a dental hand piece, comprising:
    a fluid path extending from a source of pressurized fluid to a dental hand piece;
    an operator controllable device disposed in connection with the fluid path and operable by an operator for controlling delivery of a flow of a pressurized fluid along the fluid path to the hand piece to provide a motive force for driving an operative element thereof;
    a patient controllable interrupt device disposed in connection with the fluid path and operable by a patient for interrupting the flow of the pressurized fluid along the fluid path from the pressurized fluid source to the hand piece and for venting the pressurized fluid from a portion of the fluid path between the patient interrupt device and the hand piece for reducing the motive force driving the operative element of the hand piece; and
    a reset device disposed in connection with the fluid path and operable by the operator for allowing the flow of pressurized fluid to resume along the fluid path between the pressurized fluid source and the hand piece.

2. The system of claim 1, wherein the hand piece includes an inlet port and an exhaust port, and the pressurized fluid is delivered to the hand piece through the inlet port, and when the patient controllable interrupt device is operated for interrupting the flow of pressurized fluid along the fluid path, the inlet port will be depressurized.

3. The system of claim 1, further comprising
a patient input device configured so as to be operable by the patient for outputting a patient interrupt signal;
a reset input device configured so as to be operable by the operator for outputting a reset signal; and
a signal controlled valve in operative communication with the patient input device and the reset input device and disposed in connection with the fluid path between the source of pressurized fluid and the hand piece, the signal controlled valve being configured so as to be controllably operable in response to the patient interrupt signal for moving to a first position for interrupting the pressurized fluid flow in the path and diverting at least a portion of the pressurized fluid flow from the fluid path and remaining in the first position until the reset signal is received.

4. The system of claim 3, wherein the signal controlled valve is a three port electromechanical valve.

5. The system of claim 3, wherein the signal controlled valve is a three port solenoid valve with latching capability.

6. The system of claim 3, wherein the patient input device is a hand held switch.

7. The system of claim 3, wherein the signal controlled valve is further configured so as to be controllably operable in response to the reset signal for moving to a second position for allowing the flow of pressurized fluid to resume along the fluid path between the pressurized fluid source and the hand piece.

8. The system of claim 3, wherein the operator controlled device, the patient input device and the reset input device are separate devices.

9. The system of claim 3, comprising a wireless network and wherein the patient input device and the reset input device are remote control devices, and the patient interrupt signal and the reset signal comprise wireless signals.

10. A method for delivering pressurized fluid to a dental hand piece comprising the steps of:
providing a fluid path extending from a source of pressurized fluid to a dental hand piece;
providing an operator controllable device disposed in connection with the fluid path and operable by an operator for controlling delivery of a flow of pressurized fluid along the fluid path to the hand piece to provide a motive force for driving an operative element thereof;
providing a patient controllable interrupt device disposed in connection with the fluid path and configured so as to be operable by a patient for interrupting the flow of pressurized fluid along the fluid path between the pressurized fluid source and the hand piece and venting the pressurized fluid from a portion of the fluid path between the the patient interrupt device and the hand piece for reducing the motive force driving the operative element of the hand piece; and
providing a reset device disposed in connection with the fluid path and configured so as to be operable by the operator for allowing the flow of pressurized fluid to resume in the fluid path between the pressurized fluid source and the hand piece.

11. The method of claim 10, further comprising the steps of:
providing a patient input device configured so as to be operable by the patient for outputting a patient interrupt signal;
providing a reset input device configured so as to be operable by the operator for outputting a reset signal; and
providing a signal controlled valve disposed in connection with the fluid path-between the pressurized fluid source and the the hand piece and in operative communication with the patient input device and the reset input device, the signal controlled valve being configured to be controllably operable in response to the patient interrupt signal, for
moving to a first position for interrupting the flow of pressurized fluid along the fluid path and diverting at least a portion of the flow of pressurized fluid the from the fluid path and remaining in the first position until the reset signal is received.

12. The method of claim 10, wherein the patient controllable interrupt device is a three port electromechanical valve with latching capability.

13. The method of claim 11, wherein the patient input device is a hand held switch.

14. The method of claim 11, wherein the signal controlled valve is further configured so as to be controllably operable in response to the reset signal for moving to a second position for allowing the flow of pressurized fluid to resume along the fluid path between the pressurized fluid source and the hand piece.

15. The method of claim 11, wherein the operator controlled device, the patient input device and the reset input device are separate devices.

16. A system for delivering pressurized fluid to a dental hand piece, comprising:
a fluid path extending from a source of pressurized fluid to a dental hand piece;
a tool holder disposed in connection with the fluid path and including one or more seats for holding the dental hand piece, the tool holder further including a safety stop device configured to be operable for preventing activation of an operative element of the hand piece when the hand piece is present in the seat;
an operator controllable device disposed in connection with the fluid path and operable by an operator for controlling delivery of a flow of pressurized fluid to the hand piece to provide a motive force for driving the operative element thereof;
a patient input device disposed in operative communication with the tool holder and operable by a patient for simulating presence of the hand piece in the seat of the tool holder and engaging the safety stop device for preventing continued activation of the operative element of the hand piece;
a reset input device disposed in operative communication with the tool holder and operable by the operator for disengaging the safety stop device in absence of the hand piece in the seat.

17. The system of claim 16, wherein the tool holder includes an element positionable in a first position in the seat for simulating presence of the hand piece in the seat and engaging the safety stop device and positionable in a second position simulating absence of the hand piece in the seat, and operation of the patient input device positions the element in the first position and operation of the reset input device positions the element in the second position.

18. The system of claim 16, wherein the patient input device is a hand held switch.

19. The system of claim 16, wherein the operator controlled device, the patient input device and the reset input device are separate devices.

20. The system of claim 16, further comprising a wireless network and operation of the patient input device outputs a wireless signal operable for simulating presence of the hand tool in the seat and operation of the reset device outputs a wireless signal operable for simulating absence of the dental tool in the seat.

* * * * *